United States Patent [19]

Parker

[11] Patent Number: 5,816,799
[45] Date of Patent: Oct. 6, 1998

[54] INTRAORAL ORTHOPEDIC APPLIANCE ADJUSTMENT APPARATUS

[76] Inventor: Jonathan A. Parker, 9635 29th Ave. North, Plymouth, Minn. 55441

[21] Appl. No.: 633,863

[22] Filed: Apr. 15, 1996

[51] Int. Cl.$^6$ ..................................................... A61C 5/00
[52] U.S. Cl. ............................. 433/6; 433/19; 128/848; 128/861
[58] Field of Search .................... 433/7, 18, 19, 433/24, 56, 57, 61; 600/237, 238; 128/848, 859, 861

[56] References Cited

U.S. PATENT DOCUMENTS

| | | |
|---|---|---|
| 3,798,773 | 3/1974 | Northcutt . |
| 3,835,540 | 9/1974 | Biederman ................................ 433/7 |
| 4,462,800 | 7/1984 | Jones ...................................... 433/19 |
| 4,472,139 | 9/1984 | Rosenberg ............................. 433/19 |
| 4,551,095 | 11/1985 | Mason .................................... 433/19 |
| 4,597,738 | 7/1986 | Sander et al. ............................ 433/7 |
| 4,618,324 | 10/1986 | Nord ...................................... 433/19 |
| 4,708,646 | 11/1987 | Jasper .................................... 433/19 |
| 4,713,000 | 12/1987 | Rosenberg ............................. 433/18 |
| 4,795,342 | 1/1989 | Jones ...................................... 433/19 |
| 4,901,737 | 2/1990 | Toone ................................... 128/859 |
| 4,969,822 | 11/1990 | Summer ................................. 433/19 |
| 5,267,862 | 12/1993 | Parker ................................... 433/215 |
| 5,409,017 | 4/1995 | Lowe ................................... 128/848 |
| 5,499,633 | 3/1996 | Fenton ................................. 128/848 |
| 5,566,683 | 10/1996 | Thornton .............................. 128/848 |

*Primary Examiner*—Ralph A. Lewis
*Attorney, Agent, or Firm*—Nawrocki, Rooney & Sivertson, P.A.

[57] ABSTRACT

An intraoral orthopedic appliance with adjustment apparatus and method of manufacture adjustably attaches an appliance upper dental part and lower dental part together. One appliance part is arranged to be attached to a patient's upper dental arch and the other to the patient's lower dental arch. The adjustment changes the anterior-posterior relationship of the two parts. The adjustment is provided by a pair of orthodontic screws on buccal segments of opposite sides of the dental arch which connect the two parts together to provide the adjustment. The orthodontic screws are also attached to the lower appliance part such as to provide a limited movement between the two parts. This allows the patient to move the lower jaw a limited amount with respect to the upper jaw.

6 Claims, 4 Drawing Sheets

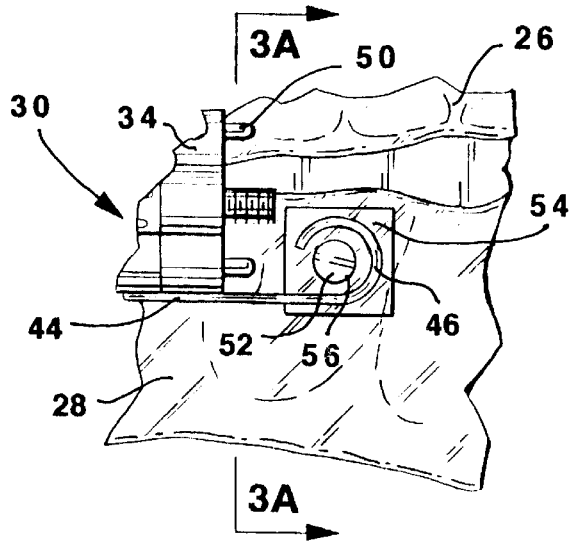 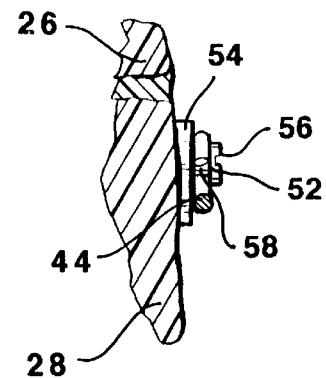
FIG.3  FIG.3A
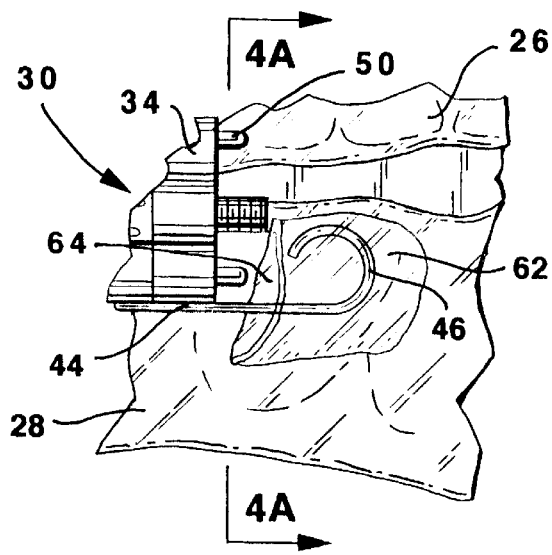 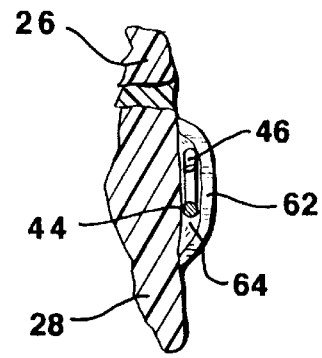
FIG.4  FIG.4A

INTRAORAL ORTHOPEDIC APPLIANCE ADJUSTMENT APPARATUS

FIELD OF THE INVENTION

This invention relates to the field of intraoral orthopedic appliances and particularly to appliances having means for adjusting the relationship between the parts after manufacture.

REFERENCE TO RELATED PATENT

This application is related to my previous U.S. Pat. No. 5,267,862 which is hereby incorporated by reference.

BACKGROUND OF THE INVENTION

The following oral appliances attached to the teeth provide a variety of means for correcting various medical problems:

In Summer, U.S. Pat. No. 4,969,822 a telescopic oral orthopedic appliance is attached to upper and lower sets of teeth by an anchor to align the upper and lower jaws for treatment of the temporomandibular joint.

In Jones, U.S. Pat. No. 4,795,342 an orthodontic device is attached to teeth of the upper and lower jaw and uses a spring module with a telescope mechanism to apply a constant calibrated force between the teeth to change their position over a period of time.

In Rosenbert, U.S. Pat. No. 4,713,000 an orthodontic appliance cemented to the teeth uses springs within cylindrical members to exert force between the teeth as a tooth movement inhibitor, inducer and controller.

In Jasper, U.S. Pat. No. 4,708,646 an orthodontic appliance for correcting an overbite or underbite is attached to some of the upper and lower teeth and uses a flexible member to exert a pushing force on the patient's upper and lower jaw.

In Nord, U.S. Pat. No. 4,618,324 an elongate interjaw-force-transferring-member terminates in loops which are fixed to teeth in different jaws. The loops extend through attachment rings in a manner to permit lateral and pivotable movement between the jaws.

In Sander et al., U.S. Pat. No. 4,597,738 an orthodontic device includes an upper and lower jaw thrust plate which are connected to the teeth and have activating rods which effect a sagittal displacement of the jaws relative to each other. The upper or lower thrust plate includes two sections connected by a jackscrew mechanism with activating rods secured thereto.

In Mason, U.S. Pat. No. 4,551,095 a Herbst mechanism is attached to the maxillary arch by a headgear tube and also connected to the mandibular arch to exert a corrective force therebetween.

In Rosenberg, U.S. Pat. No. 4,472,139 an orthopedic appliance has an adjustable bar attached on each side of the mouth to upper and lower molars to join the upper and lower teeth correct abnormal malocclusions.

In Jones, U.S. Pat. No. 4,462,800 an orthodontic bite jumping device is attached to orthodontic brackets affixed to the teeth of the upper and lower jaw uses a telescope mechanism to provide looseness in the connection.

In Northcutt, U.S. Pat. No. 3,798,773 a device secured to some of the upper and lower teeth has spring arrangements to assist the patient in moving upper segments of teeth rearwardly and lower segments of teeth forwardly each time he closes his mouth.

All of these devices are permanently and directly attached to the teeth to provide a force between teeth for various corrections. It would be desirable to provide a removable means to adjust the position of the lower jaw with respect to the upper jaw to vary the correction provided with a predetermined small amount of movement permitted between the two for patient comfort.

SUMMARY OF THE INVENTION

This intraoral orthopedic appliance with adjustment apparatus is arranged to maintain a patient's airway in order to reduce or eliminate snoring and decrease the number of respiratory obstructive events to a normal or acceptable level. Based on the clinical research and clinical experience of practitioners using oral appliances, it is clear that these devices have a positive effect on upper airway patency. Current investigation of the mode of action of these devices seems to indicate that the appliances act by anatomical repositioning, stabilization of the hard and soft tissues, and increased tonicity of the genioglossus muscle.

Adjustability of the appliance appears to be an important factor in maintaining patient comfort and is also important to the success of the appliance treatment. This refers to the ability to adjust the mandibular treatment position in order to maintain comfort and maximize the therapeutic effect.

Freedom of mandibular movement can be an important issue, especially in patients who have a tendency for clenching or bruxism. In addition, mandibular mobility while the appliance is in place, may enhance comfort of the muscles of mastication and the TMJs.

This adjustable intraoral orthopedic appliance and method of manufacture uses two parts, which are prepared using the methods described in my U.S. Pat. No. 5,267,882. These parts are arranged to respectively enclose and grip the upper and lower dental arch of a patient. The present invention apparatus attaches and adjusts the anterior and posterior locations of these two parts with respect to each other and similarly move the enclosed dental arches. Since this adjustment permits changing the relationship between the two parts at any time, this greatly simplifies obtaining a correct and comfortable fit, particularly in correcting such things as apnea where the extension of the lower jaw with respect to the upper jaw is critical.

In existing appliances, where the parts are held together by adhesive with no adjustment means being provided, the parts must be broken apart and reattached until a correct relationship between the parts is obtained. This can only be accomplished by a dentist or dental technician in an office having the necessary instruments and adhesives.

The existing appliances, described in the background of the invention, being directly attached to the teeth are not suitable candidates for use for sleep related disorders where the appliance is worn only during sleep periods. These existing appliances in general are related to teeth displacement disorders where a force must be exerted to reposition the teeth to a preferred relationship orthodontic in nature and not to such problems as obtaining a desired lower jaw extension orthopedic in nature.

The adjustment means provided by the present invention can be accomplished by the dentist or the patient with no equipment being required other than a mating adjusting tool. This permits the patients to make any number of successive adjustments themselves in their own home, after consulting with their dentist, until the desired results are finally obtained. The desired results not only includes a proper lower jaw extension but also a comfortable fit. Since the patients themselves can make any number of adjustments, this greatly improves the ability to obtain the required results with no additional cost and minimal office visits with the professional.

As discussed earlier, a fixed relationship of the two appliance parts has also proven to be quite uncomfortable for the patient. This is accentuated when the appliance must be worn for an extended period of time. The present invention provides an adjustable attachment means which has a small degree of freedom of motion between the two parts. This freedom to move the two parts a small amount improves the patient's comfort greatly. The improvement in comfort level, when the appliance must be worn for an eight hour period of time, is particularly appreciated by the patient.

This invention provides apparatus to adjustably attach two appliance parts together. These two parts comprise a lower part, which is attached around and to a patient's lower dental arch, and an upper part, which is attached around and to a patient's upper dental arch. These parts can be provided by adapting existing appliances, or can be provided by manufacturing the two parts following my U.S. Pat. No. 5,267,862, with the adjustment apparatus of the present invention connecting the two parts together. A requirement of these parts, which even though removable by the patient, must grip the respective dental arches tightly enough to provide a secure attachment means.

The connection apparatus may comprise opposed orthopedic screw mechanisms positioned on the buccal segments on opposite sides of the dental arches. Each orthopedic screw mechanism has opposed outwardly extending wires with one wire being attached to each part. These opposed wires are extended or withdrawn simultaneously by an adjusting screw. When the appliance is in place in the patient's mouth, one wire is attached to the upper appliance part and another wire is attached to the lower appliance part. With this arrangement successively adjusting the orthopedic screw mechanisms on each side of the arch moves the lower appliance part and enclosed lower jaw in an anterior or posterior direction with respect to the upper appliance part and enclosed upper jaw for adjustment.

The ends of the wires extending outwardly from the orthopedic screw mechanisms are formed into loops. In a first embodiment the loops on each side are attached directly to the parts by a suitable adhesive.

In a second embodiment threaded posts and mating threaded receptacles are used to attach the wires from each orthopedic screw mechanism to the lower appliance part. The receptacles are first attached to the lower appliance part by a suitable adhesive. After the adhesive has hardened the post is extended through the wire loop and screwed into the mating receptacle. The post itself is made smaller than the loop but with a head larger than the loop. This prevents pulling the loop over the post head and secures the wire to the lower appliance part.

Since the size of the posts are smaller than the size of the loops, this also provides a limited amount of movement between the lower wires and the lower appliance part. This allows the patient to move the upper and lower appliance parts a small amount with respect to one other. The amount of this movement can be varied by changing the amount of slack in the loop around the post. The amount of this movement can also be changed by changing the amount the post is screwed into the receptacle, since reducing the spacing between the head and the receptacle will also reduce the movement between the loop and the receptacle. This method of attachment also permits readily separating the two appliance parts for cleaning by simply unscrewing the post from the receptacle.

In a third embodiment loops are again formed in the ends of the wires and wires are attached to the upper appliance part using a suitable adhesive. The loops for the lower appliance part are first covered by wax, and then a cold-cured acrylic resin is bonded over the wax and each loop and attached to the lower appliance part, such as to form pockets around the loops with an opening in one end for the wire extending from the loop to the appliance.

The wax around the loops ensures that the pockets formed are slightly larger than the loops. The pocket opening is made smaller than the loop but larger than the wire to permit the wire to extend through the opening but retain the loop within the pocket.

After the acrylic resin has set, the wax around the lower wire loops is melted and drained from the pockets. Since the openings in the pockets are smaller than the lower loops, the loops cannot be pulled through the pocket openings, which secures the wires to the appliance lower part. Since the pockets are made slightly larger than the loops, because of the wax coating, a small amount of movement between the wire loops and the appliance part is also possible. This allows the patient to move the upper and lower appliance parts a small amount with respect to one other. The amount of this movement can also be varied by changing the thickness of the wax coating on the loops.

BRIEF DESCRIPTION OF THE DRAWINGS

Other objects of the present invention and many of the attendant advantages will be readily appreciated as the same becomes better understood by reference to the following detailed descriptions when considered in connection with the accompanying drawings, in which like reference numerals designate like parts throughout the figures thereof and wherein:

FIG. 3 shows a plan view of a detail of the wire attachment to the lower appliance part by a post extending through a loop screwed into a receptacle;

FIG. 3A shows a cross-section taken along 3A—3A of FIG. 3;

FIG. 4 is a plan view of the wire attachment to a lower appliance part by a pocket;

FIG. 4A is a cross-section taken along 4A—4A of FIG. 4; and

DETAILED DESCRIPTION OF THE INVENTION

Figure 1:
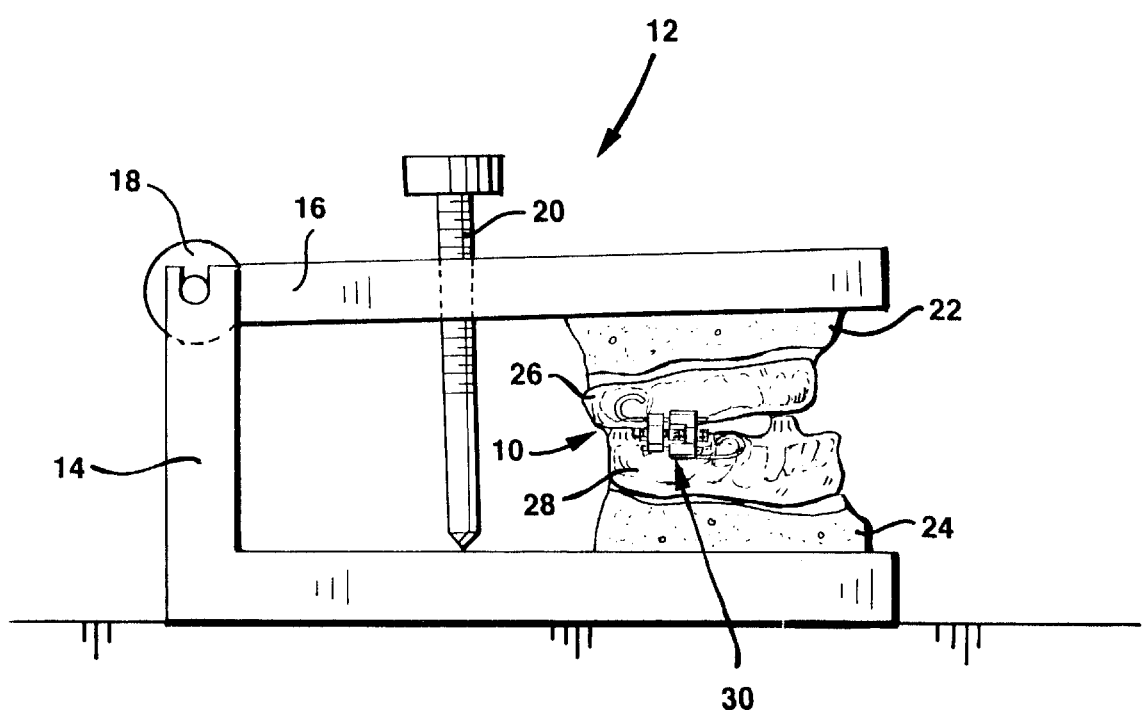
FIG. 1 illustrates the appliance mounted upon a dental articulator.

An adjustable intraoral orthopedic appliance 10 is shown mounted on dental articulator 12 in FIG. 1. The appliance parts are constructed in accordance with my U.S. Pat. No. 5,267,862 and interconnected using the present invention as described below.

Articulator 12 has a lower bow 14 and an upper bow 16 with an interconnecting hinge joint 18 to permit rotating the upper bow with respect to the lower bow. A threaded bolt 20 extends through a mating threaded hole in upper bow 16 to permit an accurate adjustment of the spacing of upper bow 16 with respect to lower bow 14.

A maxillary cast 22 and a mandibular cast 24, taken from a patient's dental arches, are mounted respectively on upper bow 16 and lower bow 14. Appliance 10 has an upper part 26 mounted over maxillary cast 22 and a lower part 28 mounted over mandibular cast 24. This apparatus and procedure are the same as those described in my previous invention. Posts 29 may be added on opposite sides of the dental arch to lower part 29 to provide a minimum airway opening.

After the upper part 26 and lower part 28 are located optimally using threaded bolt 20, orthopedic screw mechanism 30 is then attached to these two parts using a suitable adhesive. A number of adhesives suitable for this attachment, and later described attachments, are well known in the art. A number of orthopedic screw mechanisms 30, suitable for this application, are also well known in the art.

Figure 2A:
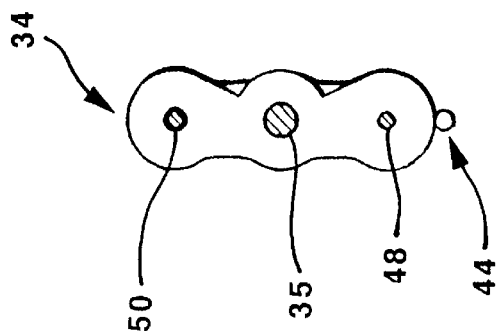
FIG. 2A shows a cross-section taken along 2A—2A of FIG. 2.
Figure 2:
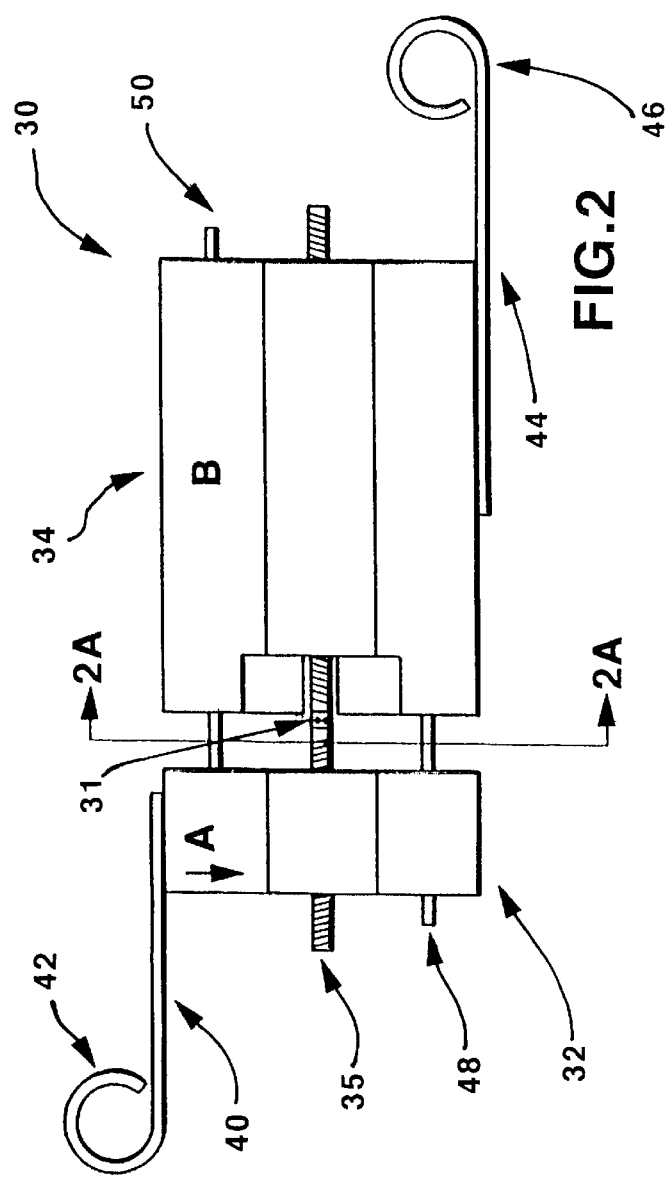
FIG. 2 shows a plan view of an orthopedic screw mechanism.

Orthopedic screw mechanism 30, shown in detail in FIG. 2, which provide adjustment means consists of two major parts, a part A 32 and a part B 34, with the spacing therebetween established by adjusting screw 35. Threads on opposite ends of screw 35 are opposite in inclination such that a rotation of the screw in one direction will move part A 32 closer to part B 34 and a rotation of the screw in the opposite direction will move part A away from part B. An arrow on part A indicates the direction to turn the screw to move part A away from part B.

Figure 2B:
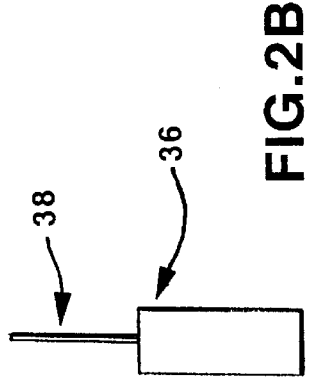
FIG. 2B shows an adjusting tool oriented correctly with respect to the mechanism of FIG. 2 to engage the orthopedic screw mechanism.
Figure 5:
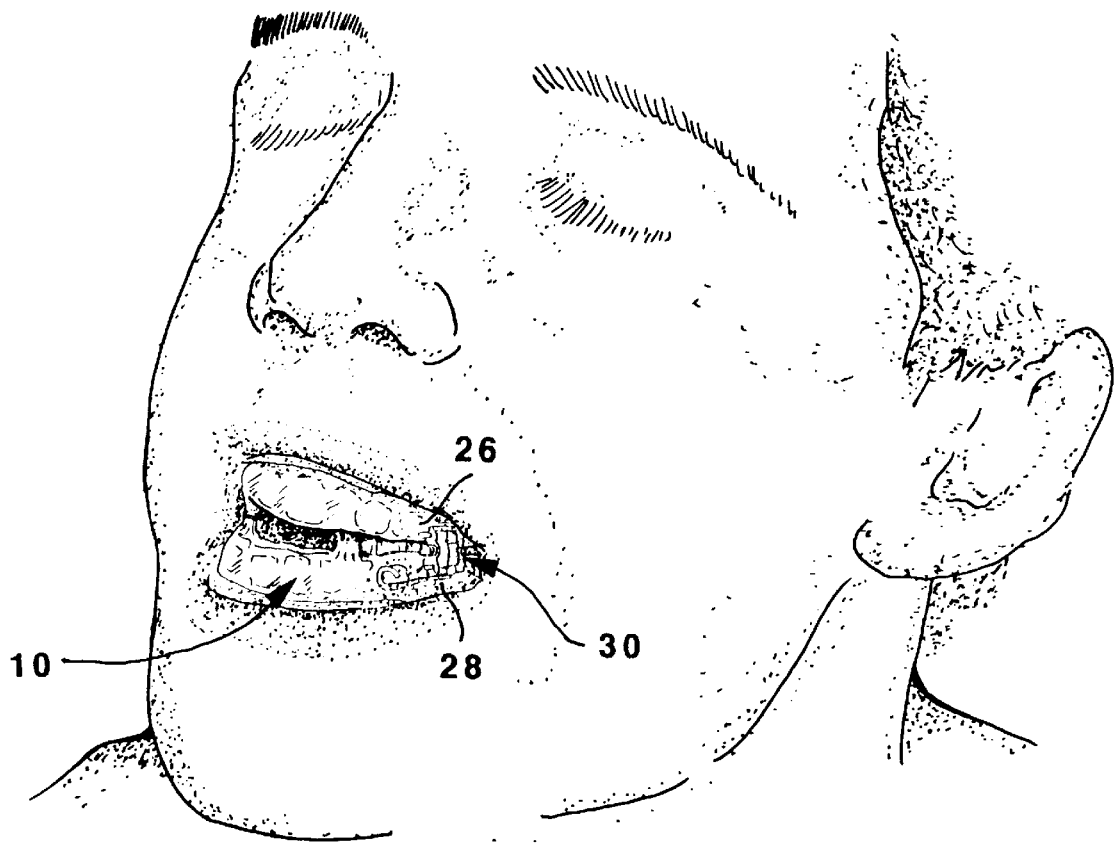
FIG. 5 is a view of the appliance mounted within a patient's mouth.

Screw 35 has a set of radially directed holes 31 evenly spaced around its periphery for rotating the screw. Adjusting tool 36, shown in FIG. 2B has a cylindrical shaped extension 38 sized to fit within holes 31 in order to rotate screw 35. The portion of body B 34 immediately adjacent to screw 35 is cut back to allow a greater adjustment angle for tool 36. When tool 36 is inserted into one of the exposed holes 31, it can be used to rotate adjusting screw 35 to move part A 32 and part B 34 either closer together or further apart depending upon the direction screw 35 is rotated.

Wire 40, which has loop 42 formed in its outer end, is connected to part A 32. Wire 44, which has loop 46 formed in its outer end is connected to part B 34. Guide pin 48, which extends into and is attached to part B 34, extends slideably through an aligned hole in part A 32. Guide pin 50, which extends within and is attached to part A 32, extends slideably through an aligned hole in part B 34. Guide pins 48 and 50 maintain the orientation of part A 32 with respect to part B 34.

In a first embodiment loops 42 and 46 are respectively attached to body A 32 and body B 34 on both sides of the dental arch by an adhesive. This attachment means is illustrated in FIG. 1 for one side of the arch.

In a second embodiment the end loops 42 and 46 of wires 40 and 44 are attached to the lower part 28 of appliance 10, as shown in detail in FIGS. 3 and 3A for loop 46 which provide past and receptacle means. Here threaded bolt 52 extends through loop 46 into a mating threaded hole in planar receptacle 54. Receptacle 54 is attached to lower part 28 by an adhesive. Bolt 52 has a head 56 larger than loop 46 and a shank 58 smaller than the loop. Shank 58 being smaller than loop 46 provides a small amount of movement between the loop and bolt 52. This in turn allows lower part 28 to move the same amount with respect to upper part 26 of appliance 10. The spacing between shank 58 and loop 56 can be varied to vary the amount of freedom between lower part 28 and upper part 26.

In a third embodiment the end loops 42 and 46 of wires 40 and 44 are attached to the lower part 28 of appliance 10, as shown in detail in FIGS. 4 and 4A, for loop 46. A cold-cured acrylic resin of a mixed polymer and monomer, which readily adheres to lower part 28, is formed over loop 46 such as to form a loop against the lower part. An opening 64, is also formed into pocket 62 which is made large enough to allow wire 44 to extend outward from the pocket but is made smaller than loop 46 to capture the loop within the pocket. Since pocket 62 loosely encloses loop 46 a small amount of motion between the loop and plastic sheet 62 is provided. This also allows lower part 28 to move the same small amount with respect to upper part 26. The amount of this movement can be changed by changing the size of the pocket with respect to the loop.

As an aid to forming pocket 62 with the desired looseness with respect to loop 46, the loop can be coated with wax before the cold-cured acrylic is attached to lower part 28. After the acrylic has set the wax can be melted and drained from the pocket using the lost wax technique to provide the desired freedom of motion of the loop within the pocket.

The material used here for the pockets can be any plastic which will provide the necessary strength to secure the wire loop. The orthopedic screw mechanism described is merely illustrative of a screw adjustment arrangement which will provide the necessary range of adjustment along with automatic locking of the adjusted position. The adhesives can be any number of commercially available adhesives developed for dental use. The means of obtaining a limited freedom of motion between the two appliance parts is likewise merely illustrative. Any connection which will provide a small but limited motion between the two parts will suffice.

This adjusting mechanism which permits an adjustment of the upper and lower parts of an appliance relative to each other after manufacture provides an effective means of obtaining a desired repositioning of the two parts without disassembly. Previous appliances required disassembling and reassembling in order to obtain a new position of the parts relative to each other.

The fact that the patient themselves can make the adjustment provides the only effective adjustment means which can really provide effectiveness and patient comfort. Any adjustment in an office simply cannot be tested over time to determine the comfort and effectiveness of the parts placement and position of the lower jaw. When the patient makes the adjustment, this adjustment can be tested over time, and an uncomfortable fit, or one that does not solve the problem addressed, can readily be changed and tested again until the optimum arrangement is obtained. This can be accomplished by consulting with the dentist by phone with a minimal number of office visits.

The freedom of motion between the two appliance parts greatly increases the comfort of the patient. The patient may experience discomfort in the jaw area when the appliance grips the teeth and holds the lower jaw in a fixed relationship for a long period of time. The ability to move the two parts a small distance, which is lacking in other appliances, greatly improves the patient comfort when the appliance is worn for a long period of time, such as overnight, which is required for a number of sleep related problems.

The placement of the adjustable screw mechanism on the buccal segments on opposite sides allow incremental adjustment of the jaw position without impinging or reducing the space available for the tongue. This is important in correcting for problems such as apnea where displacing the tongue will constrict the flow of air and add to the problem.

While this invention has been described with respect to specific embodiments, these descriptions are not intended to be construed in a limiting sense. Various modifications of the illustrative embodiments, as well as other embodiments of the invention, will be apparent to persons skilled in the art upon reference to these descriptions. It is therefore contemplated that the appended claims will cover any such modifications or embodiments as fall within the true scope of the invention.

I claim:

1. Intraoral orthopedic appliance apparatus for adjusting an upper dental arch with respect to a lower dental arch comprising:
    a) an upper appliance part sized to fit over and grip an upper dental arch and a lower appliance part sized to fit over and grip a lower dental arch;
    b) first and second adjustment means having opposing parts with adjustable spacing which can be varied in spacing for adjusting the anterior-posterior position of the upper appliance part with respect to the lower appliance part;
    c) first and second post and receptacle means having a post and larger encircling receptacle interposed between said lower appliance part and said first and second adjustment means respectively with the receptacles of each said receptacle means being connected to said attachment means for providing a limited predetermined amount of freedom of motion therebetween; and
    d) adhesive means for attaching the part of said first and second adjustment means opposite said post and receptacle means to the upper appliance part and for attaching the post to the lower appliance part at buccal segments and on opposite sides of the dental arch.

2. Apparatus as in claim 1 further comprising:
    a) said first and second adjustment means each having at least a first and second wire extending outwardly therefrom in opposite directions, with the distal ends of the respective second wires from each adjustment means terminating in a loop, the first wires from said first and second adjustment means being attached to the upper appliance part by said adhesive means;
    b) said receptacle means having two generally planar receptacles each having a threaded hole extending therethrough generally perpendicular to the planar surfaces, one planar surface of each receptacle being attached to the lower appliance part by said adhesive means with the receptacles being positioned such that each threaded hole is positioned adjacent to and generally centered on one of the loops at the distal end of the second wires; and
    c) two posts each having a head and a shank, each shank being sized and threaded to mate with the threaded holes in the receptacles, the shank having a smaller diameter and the head having a larger diameter than the diameter of the wire loops such that the posts can be inserted through the loops of said second wires and the shank threaded into a hole in an adjacent receptacle to secure the respective second loops to the lower appliance part with a predetermined freedom of motion determined by the difference between the diameters of the loop and the shank.

3. Intraoral orthopedic appliance apparatus for adjusting an upper dental arch with respect to a lower dental arch comprising:
    a) an upper appliance part sized to fit over and grip an upper dental arch and a lower appliance part sized to fit over and grip a lower dental arch;
    b) first and second adjustment means having opposing parts with adjustable spacing which can be varied in spacing for adjusting the anterior-posterior position of the upper appliance part with respect to the lower appliance part;
    c) first and second pocket means having a wire terminating in a loop and having a pocket enclosing the loop with the wire portion opposite the loop being attached to said adjustment means interposed between said lower appliance part and said first and second adjustment means respectively for providing a limited predetermined amount of freedom of motion therebetween; and
    d) first adhesive means for attaching the part of said first and second adjustment means opposite pocket means to the upper appliance part and for attaching said pocket to the lower appliance part at buccal segments and on opposite sides of the dental arch.

4. Apparatus as in claim 3 further comprising:
    a) said first and second adjustment means each having at least a first and second wire extending outwardly in opposite directions therefrom, with the distal ends of the second wires terminating in a loop, and with each first wire from said first and second adjustment means being attached to the upper appliance part by said adhesive means;
    b) said pocket means being formed into two pockets over the loops of each second wire attaching said second wire to the lower appliance part such that each second loop is oriented generally parallel to the adjacent outer surface of the lower appliance part, the pockets being a predetermined amount larger in size than the enclosed loops, the pockets each having an opening providing access for a second wire oriented generally parallel to the plane of the enclosed loop, the openings being smaller than enclosed loop and larger than the wire such that each loop can move a predetermined amount within its respective pocket but cannot be pulled through the pocket opening.

5. The method of producing an apparatus to adjust an upper dental arch with respect to a lower dental arch comprising:
    a) providing:
        i) an articulator;
        ii) adhesive means;
        iii) an upper appliance part sized to fit over and grip an upper dental arch and a lower appliance part sized to fit over and grip a lower dental arch;
        iv) first and second adjustment means for adjusting the anterior-posterior position of the upper appliance part with respect to the lower appliance part; said first and second adjustment means each having at least a first and second wire extending outwardly in opposite directions therefrom, with the distal ends of the second wires each terminating in a loop;
        v) two generally planar receptacles each having a threaded hole extending therethrough generally perpendicular to the planar surfaces;
        vi) two posts each having a head and a shank, each shank being sized and threaded to mate with the threaded holes in the receptacles, the shank having a smaller diameter and the head having a larger diameter than the diameter of the wire loops;

b) placing said appliance parts upon said articulator and setting the articulator for proper positioning of said parts;

c) attaching the first wires of the adjustment means by said adhesive means to the upper appliance parts with the first and second adjustment means extending between the upper and lower appliance parts at buccal segments and on opposite sides of the dental arch and with the wire loops from the second wires extending generally parallel to and adjacent to the lower appliance part;

d) attaching a planar surface of each receptacle to the lower appliance part by said adhesive means with each hole oriented generally perpendicular to the adjacent appliance part and with each hole positioned adjacent to and generally centered on a loop from a second wire; and e) inserting the shank of a post through each of the second loops and threading the shank into the opposed receptacle.

6. The method of producing an apparatus to adjust an upper dental arch with respect to a lower dental arch comprising:

a) providing:
   i) an articulator;
   ii) adhesive means;
   iii) an upper appliance part sized to fit over and grip an upper dental arch and a lower appliance part sized to fit over and grip a lower dental arch;
   iv) first and second adjustment means for adjusting the anterior-posterior position of the upper appliance part with respect to the lower appliance part; said first and second adjustment means each having at least a first and second wire extending outwardly in opposite directions therefrom, with the distal ends of the second wires from each adjustment means terminating in a loop; and
   vi) wax b) placing said parts upon said articulator and setting the articulator for proper positioning of said parts;

c) attaching the first wires of the adjustment means by said adhesive means to the upper appliance parts with the first and second adjustment means extending between the upper and lower appliance parts at buccal segments and on opposite sides of the dental arch and with the wire loops from the second wires extending generally parallel to and adjacent to the lower appliance part;

d) placing a layer of wax over each loop;

e) forming the adhesive means into pockets over the loops such as to attach the wax enclosed loops to the lower appliance with the plane of each enclosed loop oriented generally parallel to the adjacent outer surface of the lower appliance, each pocket having an opening formed therethrough which is generally parallel to the plane of the enclosed loop, with the second wires from an enclosed loop extending therethrough, each opening being smaller than the enclosed loop and larger than the extending second wire;

g) allowing the adhesive to harden; and i) melting the wax from around said loops and draining the melted wax from each pocket.

* * * * *